United States Patent [19]
Tanji et al.

[11] Patent Number: 5,344,516
[45] Date of Patent: Sep. 6, 1994

[54] METHOD FOR FORMING A SKIN-CONTACTING TOPSHEET OF A DISPOSABLE DIAPER WITH AN ELASTIC OPENING

[75] Inventors: Hiroyuki Tanji; Ichiro Wada; Yoshio Ono; Hiroyuki Soga, all of Kawanoe, Japan

[73] Assignee: Uni-Charm Corporation, Ehime, Japan

[21] Appl. No.: 44,385

[22] Filed: Apr. 7, 1993

[30] Foreign Application Priority Data

Apr. 17, 1992 [JP] Japan ................... 4-124284

[51] Int. Cl.⁵ .................... A61F 13/15; B32B 31/00
[52] U.S. Cl. ................... 156/164; 156/160; 156/204; 156/221; 156/226; 156/227; 156/256; 156/265; 156/267; 156/229; 604/385.1; 604/385.2
[58] Field of Search ............... 156/229, 164, 160, 163, 156/265, 494, 495, 519, 204, 199, 221, 226, 227, 256, 264, 267; 604/385.2, 385.1

[56] References Cited

U.S. PATENT DOCUMENTS

| 4,595,441 | 6/1986 | Holvoet et al. ............. 156/265 |
| 4,662,877 | 5/1987 | Williams ................... 604/385.2 |
| 4,704,116 | 11/1987 | Enloe ..................... 604/385.2 |
| 4,892,536 | 1/1990 | DesMarais et al. ......... 604/385.2 |
| 4,915,767 | 4/1990 | Rajala et al. ............. 156/229 X |
| 4,990,147 | 2/1991 | Freeland .................. 604/385.2 |
| 5,037,416 | 8/1991 | Allen ..................... 604/385.2 X |
| 5,110,386 | 5/1992 | Ochi et al. ............... 604/385.1 X |

FOREIGN PATENT DOCUMENTS

| 0200482 | 11/1986 | European Pat. Off. |
| 0391476 | 10/1990 | European Pat. Off. |
| 0486006 | 5/1992 | European Pat. Off. |
| 508477 | 10/1992 | European Pat. Off. ...... 604/385.2 |
| 2668364 | 4/1992 | France. |
| 49-120439 | 10/1974 | Japan ..................... 156/164 |

*Primary Examiner*—Jeff H. Aftergut
*Attorney, Agent, or Firm*—Fred Philpitt

[57] ABSTRACT

A method for forming a skin-contacting topsheet of disposable diaper with an elastic opening, wherein the opening 16 formed in the skin-contacting topsheet of a disposable diaper is elasticized along its whole peripheral edge and reinforced so as to form uniform gathers along the whole peripheral edge.

The skin-contacting topsheet comprises a pair of sheet members overlapping side by side and having mutually opposed inner side edges, respectively, which are provided with cutouts so that each pair of mutually opposed cutouts form each opening, then elastic members are provided along halves of the opening's whole peripheral edge and these elastic members are covered with a part of the skin-contacting topsheet.

2 Claims, 2 Drawing Sheets

FIG. I
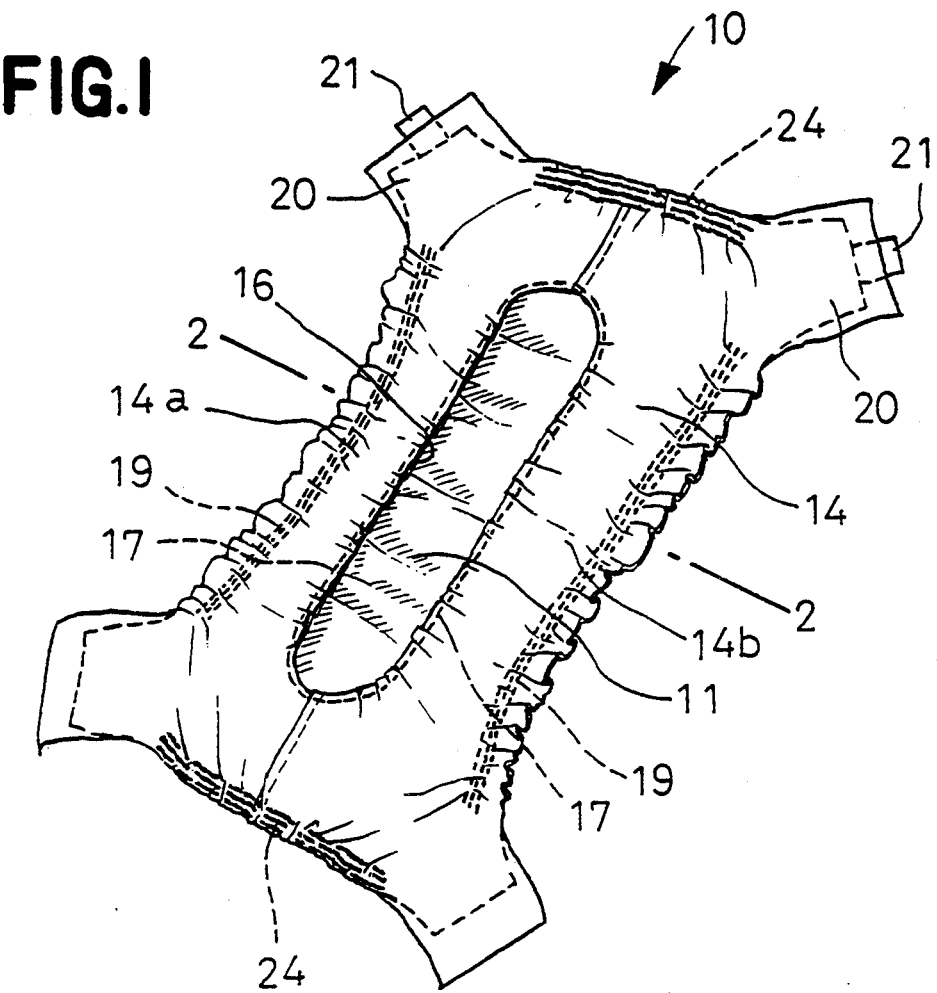
FIG. 2
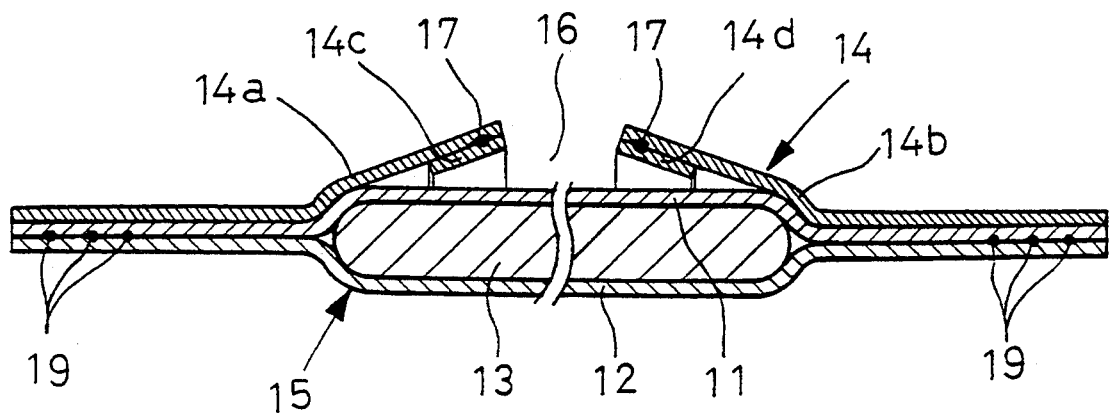

METHOD FOR FORMING A SKIN-CONTACTING TOPSHEET OF A DISPOSABLE DIAPER WITH AN ELASTIC OPENING

BACKGROUND OF THE INVENTION

This invention relates to a method for forming a skin-contacting topsheet of a disposable diaper with an elastic opening for reliable introduction of excretions.

Japanese Utility Model Application Disclosure Gazette No. 1974-120439 discloses a diaper-cover having a topsheet formed at its central zone with an opening extending longer in the longitudinal direction than in the transverse direction of the topsheet, wherein the opening is provided along its peripheral edge with a longitudinally stretchable elastic member so as to define a closed loop-shaped elastic line. Japanese Patent Application Disclosure Gazette No. 1986-41304 also discloses a disposable diaper having a topsheet formed at its central zone with an opening extending longer in the longitudinal direction than in the transverse direction of the topsheet, wherein the opening is provided along its laterally opposite side edges with elastic members, respectively.

With these diaper-cover and diaper both having the openings, excretions flow through said opening into pockets defined between said topsheet and a separately provided topsheet underlying the first-mentioned topsheet and is held therein, making it possible to avoid or at least alleviate apprehension that the wearer's skin might be smeared with excretions spreading over the skin-contacting uppermost topsheet, give the wearer unpleasant feeling and even cause the wearer to be attacked with a skin disease.

The above-identified Japanese Utility Model Application Disclosure Gazette No. 1974-120439 and Japanese Patent Application Disclosure Gazette No. 1986-41304 both disclose neither a method for forming the skin-contacting topsheet with the opening nor a method for attaching the elastic member around the opening. According to the former, it is supposed that the whole peripheral edge of the opening is provided with an elastic member in the endless fashion and then said elastic member is covered with the peripheral portion of the opening. However, no specific method is found in the specification. In view of the fact that the former relates to a reusable diaper-cover, the method probably employs the cutting and sewing techniques well known in the art. According to the latter, the central portion of the sheet is cut away to form the opening and both side edges of the opening are provided with the respective elastic members bonded to rear sides of the respective side edges with use of adhesive. Consequently, the diaper provided by the latter is not only unseemly but also poor in a desired strength along the peripheral edge of the opening because the elastic members are not covered at all although they are provided on the rear side of the sheet. Moreover, such an arrangement will not result in formation of neatly uniform gathers along the whole peripheral edge of the opening and therefore it can not be expected that the whole peripheral edge of the opening tightly bears against the wearer's skin.

It is a principal object of the invention to form a skin-contacting topsheet of a disposable diaper with an opening of which the whole peripheral edge presents the desired strength and contains therein elastic members covered with the topsheet.

SUMMARY OF THE INVENTION

The object set forth above is achieved, according to the invention, by a method for forming a skin-contacting topsheet of a disposable diaper with an elastic opening, said method comprising steps of: A. feeding a continuous elastic member maintained under elongation onto a continuous web longitudinally thereof so that the continuous elastic member describes an undulating line alternately curved toward a first side edge and then toward a second side edge of said continuous web opposed to said first side edge so as to form crests and relatively wide troughs, respectively, and bonding said continuous elastic member to said web with use of adhesive to obtain a first continuous composite web; B. folding a region of said first continuous composite web extending adjacent said first side edge thereof along a folding line longitudinally extending at a height between said first side edge and said troughs so that respective said crests are at least partially contained within a range defined between said folding line and said first side edge, followed by bonding said folded region to non-folded region of said first continuous composite web to obtain a second continuous composite web comprising said continuous elastic member covered with said continuous web; C. cutting away regions of said second continuous composite web surrounded by respective said crests, troughs and folding line to obtain a third continuous composite web thus formed with cutouts destined to define halves of the respective openings; D. placing a pair of said third continuous composite webs side by side with each pair of the associated cutouts being opposed to and aligned with each other in a transversely symmetric relationship, laying these webs upon a topsheet of a continuous diaper web comprising a plurality of individual diapers so that each pair of edge portions of the respective third continuous composite webs longitudinally extending across each pair of mutually opposed crests overlap each other, and bonding said webs along outer side edges onto the topsheet of the continuous diaper web; and E. cutting said continuous diaper web now having said pair of third continuous composite web bonded thereto transversely along lines vertically dividing said crests in halves to obtain the individual diapers.

Preferably, said step E further comprises a step of bonding each pair of edge portions of the respective third continuous composite webs longitudinally extending across each pair of mutually opposed crests to each other in an overlapping relationship.

BRIEF DESCRIPTION OF THE DRAWINGS

The invention will be described by way of example in reference with the accompanying drawings, in which:

FIG. 1 is a perspective view showing the inner side of a disposable diaper having a skin-contacting topsheet formed according to a method of the invention;

FIG. 2 is a sectional view taken along a line 2—2 in FIG. 1;

PREFERRED EMBODIMENTS OF THE INVENTION

Figure 3:
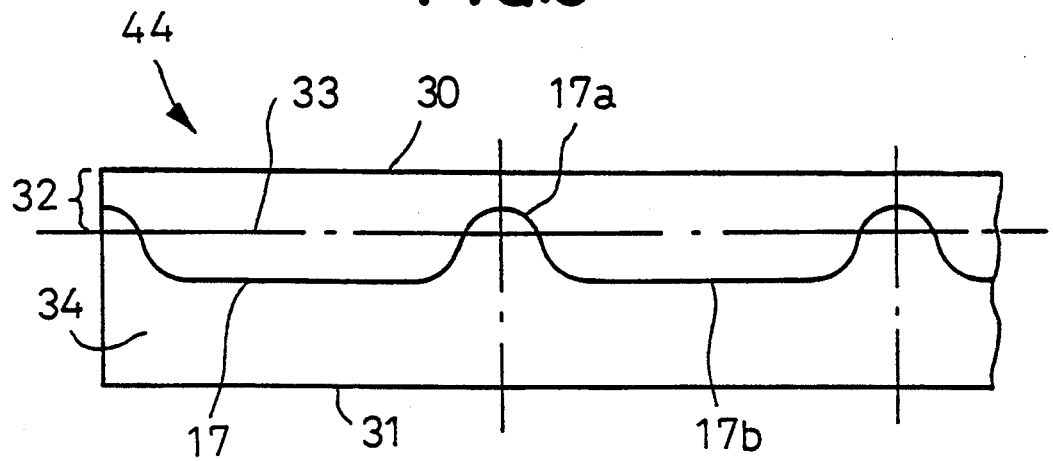
FIG. 3 is a schematic plan view illustrating the manner in which the continuous elastic member is attached to the continuous web as the starting material for the skin-contacting topsheet to form a first continuous composite web.

Referring to FIGS. 1 and 2, a diaper 10 comprises a liquid-permeable topsheet 11, a liquid-impermeable backsheet 12, a liquid-absorbent core 13 sandwiched therebetween, and a liquid-resistant skin-contacting topsheet 14. The skin-contacting topsheet 14 is centrally formed with an opening 16 which is longer in the longitudinal direction than in the transverse direction of this sheet 14 and has longitudinally opposite ends describing circular arcs, respectively. The opening 16 may be formed at least within the crotch zone.

The skin-contacting topsheet 14 actually comprises a pair of sheet members 14a, 14b overlapping side by side and having the mutually opposed inner side edges, which are provided with cutouts so that each pair of mutually opposed cutouts form each opening 16. Reinforcing sheet members 14c, 14d made of the same material as that for the sheet members 14a, 14b are bonded to edges of the respective cutouts and there are provided longitudinally stretchable elastic members 17 attached between the sheet members 14a, 14b and the reinforcing sheet members 14c, 14d along those edges of the respective cutouts with use of hot melt type adhesive (not shown). Lengths of said inner edges remaining in an overlapping relationship after the cutouts have been formed are bonded together with hot melt type adhesive (not shown).

The pair of elastic members 17 are independent of each other in contrast with the single continuous elastic member forming an endless loop as employed by the previously mentioned diaper-cover of prior art. Additionally, the inner side edges of the sheet members 14a, 14b overlapping in the proximities of the longitudinally opposite ends are bonded together utilizing hot melt type adhesive. Such arrangement allows the skin-contacting topsheet 14 to be easily torn off along said overlapping lengths of the inner side edges when it is desired to expose almost the whole surface of the topsheet underlying the skin-contacting topsheet 14 and thereby to scrape off solid excretion held between the skin-contacting topsheet 14 and the topsheet 11. While said overlapping inner side edges are bonded together utilizing said adhesive, the hot melt type adhesive used for assembling of such diaper generally has not sufficient bonding force, even after curing, to make said tearing off difficult.

Liquid excretion is introduced through the opening onto the topsheet 11, then permeates this topsheet 11 and is absorbed by the core 13 while solid excretion is introduced into pockets defined between the topsheet 11 and the skin-contacting topsheet 14. Such solid excretion can be scraped off from the topsheet 11 to the desired extent with the skin-contacting topsheet 14 having been torn off from the longitudinally opposite ends of the opening 16.

Between the laterally opposite edges of the topsheet 11 and the laterally opposite edges of the backsheet 12 both extending outward from both sides of the liquid-absorbent core 13, a plurality of elastic member 19 each comprising, in turn, a plurality of elastic threads, are attached under their stretched states with use of hot melt type adhesive (not shown), respectively, so as to be stretchable longitudinally of the sheets and fit tightly around the wearer's legs. Similarly, between the longitudinally opposite ends of the topsheet 11 and the associated ends of the backsheet 12, there are provided a plurality of elastic members 24 each comprising, in turn, a plurality of elastic threads, respectively, so as to be stretchable transversely of the sheets and fit tightly around the wearer's waist.

The topsheet 11 may be made of nonwoven fabric, porous plastic film or the like, the backsheet 12 may be made of plastic film, laminated sheet of this plastic film and nonwoven fabric or the like, the liquid-absorbent core 13 may be made of a mixture of fluff pulp and high absorption polymer powder or the like. The skin-contacting topsheet 14 and the reinforcing sheet members 14c, 14d are preferably made of water-repellent and high air-permeable nonwoven fabric. It should be understood that, in this description of the invention, the "liquid-resistant" material refers to the material having a sufficient degree of water-repellence to prevent liquid excretion from easily penetrating therethrough with the diaper being worn on the wearer's body.

Referring to FIG. 1, the diaper 10 has two pairs of wing-like flaps 20 extending outward form the laterally opposite sides of the waist line, respectively, and free ends of tape fasteners 21 attached to the respective rear side wing-like flaps 20 may be adhesively secured to the backsheet 12 on the front side to erect the diaper 10 around the wearer's body.

Now the method of the invention will be described by way of example with reference to FIGS. 3 through 5.

Referring to FIG. 3, a continuous elastic member 17 maintained under elongation is fed by transverse means (not shown) onto a continuous web 34 longitudinally thereof so that the continuous elastic member 17 describes an undulating line alternately curved toward a first side edge 30 and then toward a second side edge 31 of the continuous web 34 opposed to said first side edge 30 so as to form crests 17a and relatively wide troughs 17b, respectively, and bonded to the web 34 with use of hot melt type adhesive (not shown) to obtain a first continuous composite web 44.

Figure 4:
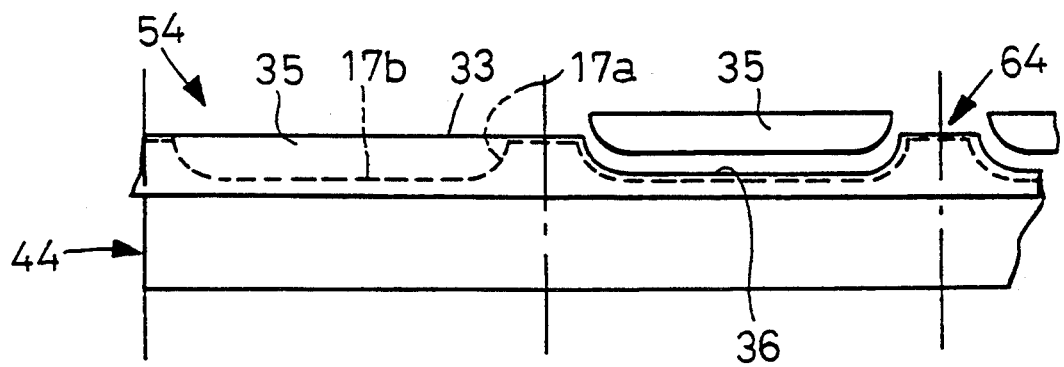
FIG. 4 is a schematic plan view illustrating the manner in which said continuous web is partially folded back to cover said continuous elastic member so as to form a second continuous composite web, followed by cutting away the portions surrounded by said elastic member so as to form a third continuous composite web.

Referring to FIGS. 3 and 4, region 32 of the first continuous composite web 44 extending adjacent the first side edge 30 thereof is folded along a folding line 33 longitudinally extending between the first side edge 30 and the troughs 17b so that the respective crests 17a are at least partially contained within a range defined between the folding line 33 and the first side edge 30. This folded region 32 is then bonded to a non-folded region of the first continuous composite web 44 to obtain a second continuous composite web 54 comprising the continuous elastic member 17 covered with the continuous web 34.

Regions 35 of the second continuous composite web 54 which are surrounded by the respective crests 17a, troughs 17b and folding line 33 are cut away to obtain a third continuous composite web 64 thus formed with cutouts 36 destined to define halves of the respective openings 16.

Figure 5:
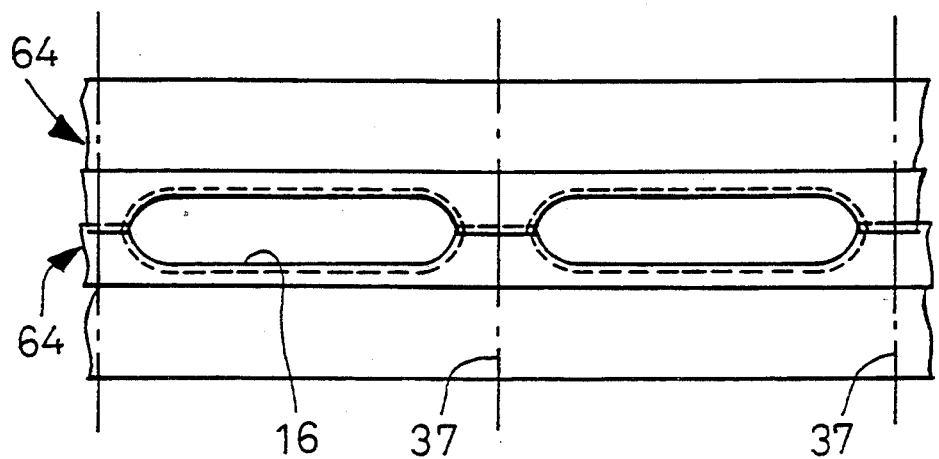
FIG. 5 is a schematic plan view illustrating a manner in which a pair of said third continuous composite webs are placed side by side in overlapping relationship.

Referring to FIG. 5, a pair of the third continuous composite webs 64 are placed side by side with each pair of the associated cutouts 36 being opposed to and aligned with each other in a transversely symmetric relationship, and laid upon a topsheet of continuous diaper web (not shown) comprising a plurality of individual diapers with each pair of edge portions of the respective third continuous composite webs 64 longitudinally extending across each pair of mutually opposed crests 17a of the respective webs 64 overlapping each other. These webs 64 are then bonded along the outer side edges onto the topsheet of said continuous diaper web and said continuous diaper web now having the webs 64 bonded thereto is transversely cut along lines 37 vertically dividing the respective pairs of mutually opposed crests 17a in halves to obtained the individual diapers. The overlapping edge portions of the respective third continuous composite webs 64 extending across the respective pairs of mutually opposed crest 17a are bonded together utilizing hot melt type adhesive (not shown). It should be understood that these edge portions may be left not bonded, if desired.

Said continuous diaper web comprises a plurality of individual diapers 10 substantially as illustrated by FIG. 1 (except for absence of the skin-contacting topsheet 14) which are successively continuous with one another longitudinally thereof. The method for making such continuous diaper web is well known to those skilled in the art from various patent specifications and therefore details of such method will not be described here.

While the embodiment has been illustrated and described with respect to the so-called open-type diaper utilizing the tape fasteners to close the waist line around the wearer's body, the invention will be applicable also to so-called pants type diaper (inclusive of training pants) having a continuous waist line.

As will be readily appreciated from the foregoing description, the diaper according to the invention comprises the skin-contacting topsheet for each individual diaper cut from the third continuous composite web formed with the opening which is provided along the half peripheries thereof with a pair of mutually independent elastic members, respectively, to elasticize the whole periphery so that the gathers uniformed formed along the whole periphery of the opening may tightly bear against the wearer's skin and thereby excretions may be reliably introduced into the opening. Furthermore, the respective elastic members are covered with the folded regions which function also to reinforce the periphery of the opening, thus realizing the diaper comprising the skin-contacting topsheet formed with the opening of good appearance and high strength.

According to the invention, the skin-contacting topsheet comprises a pair of sheet members each having the cutout destined to define a half of the opening and the elastic members attached around said cutout. More specifically, these sheet members are arranged side-by-side with the respective cutouts being symmetrically opposed to and aligned with each other so as to define the opening at the central zone of the assembled skin-contacting topsheet. Such arrangement realizes the diaper having the skin-contacting topsheet adapted to be easily torn off from the longitudinally opposite ends of the opening in order to scrape off solid excretion held on the topsheet underlying said skin-contacting topsheet.

What is claimed is:

1. The method which comprises the steps of
(A) providing an elongated continuous web (34) having a first side edge (30) and a second side edge (31) as well as an elongated elastic member (17) maintained under elongation,
(B) continuously feeding said continuous web (34) and said elastic member (17) into bonding contact with each other so that the elastic member (17) follows an undulating path which alternately curves toward said first side edge (30) and then toward said second side edge (31) so as to form alternating crests (17a) and relatively wide troughs (17b), to thereby form a first continuous composite web (44),
(C) folding said first continuous composite web (44) to form a folded over portion along a longitudinal folding line (33)
  (i) which is located between said first side edge (30) and the bottom of said troughs (17b) and
  (ii) which passes through said crests (17a),
(D) bonding together said folded over portion so that said first side edge (30) is positioned closer to said second side edge (31) than is said elongated elastic member (17), whereby a second continuous composite web (54) is obtained that has said continuous elastic member (17) covered by said folded over portion,
(E) cutting away spaced apart sections of said folded over portion on each side of said crests (17a) to thereby form a third continuous composite web (64) containing a series of spaced apart cutouts (36),
(F) placing a pair of said third continuous composite webs (64) side-by-side with each pair of the associated cutouts (36) being opposed to and aligned with each other in a transversely symmetric relationship, laying these third continuous composite webs (64) upon a topsheet (11) so that the crests (17a) of the pair of said third continuous composite webs (64) at least partially overlap each other,
(G) bonding said pair of third continuous composite webs (64) resulting from step (F) onto said topsheet (11), and
(H) cutting the resulting product transversely along lines that divide the overlapped crest portions (17a) in half.

2. The method as recited in claim 1, wherein each pair of mutually opposed crests (17a) are bonded to each other in at least a partially overlapping relationship.

* * * * *